United States Patent [19]

Turner et al.

[11] Patent Number: 6,055,850
[45] Date of Patent: May 2, 2000

[54] MULTI-DIRECTIONAL PERMEAMETER

[76] Inventors: Daniel R. Turner, 981 Tularosa Ave., Lake City, Fla. 32025; Cristina S. Crawford, 7649 SW. C.R. 18, Hampton, Fla. 32044

[21] Appl. No.: 08/998,095

[22] Filed: Dec. 24, 1997

[51] Int. Cl.[7] .................................................. G01N 15/08
[52] U.S. Cl. .................................................... 73/38
[58] Field of Search ................................. 73/38, 152.07

[56] References Cited

U.S. PATENT DOCUMENTS

| | | | |
|---|---|---|---|
| 2,534,718 | 12/1950 | Leas et al. | 73/38 |
| 2,618,151 | 11/1952 | Leas | 73/38 |
| 4,715,212 | 12/1987 | Johanson | 73/38 |
| 5,161,407 | 11/1992 | Ankeny et al. | 73/38 |

*Primary Examiner*—Michael Brock
*Attorney, Agent, or Firm*—Carnes Cona & Dixon

[57] ABSTRACT

A multi-directional permeameter apparatus is disclosed for the purpose of determining the coefficients of permeability by utilizing a constant (or falling) head method for the laminar flow of a fluid, such as water, through a specific material or sample which is being tested. The apparatus includes a mold removably secured to a base. A lid is removably secured to the mold to render a device which can be used for compaction as well as testing. Inlet and outlet ports are located in the apparatus for allowing fluid flow to occur in both the horizontal plane and the vertical plane for determining the coefficients of permeability of a particular sample either horizontally, vertically, or simultaneously horizontally and vertically.

20 Claims, 4 Drawing Sheets

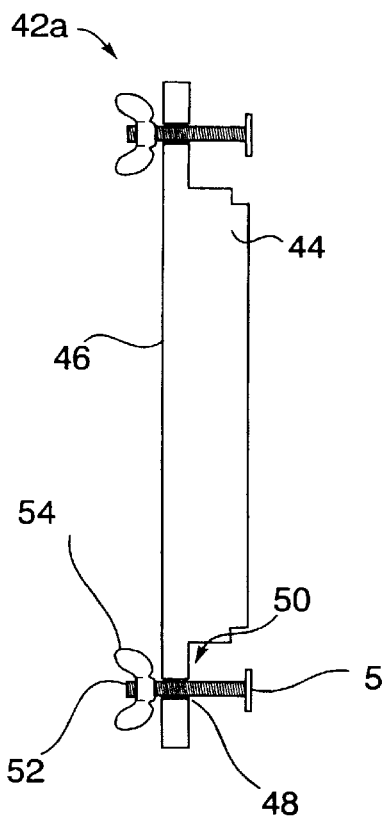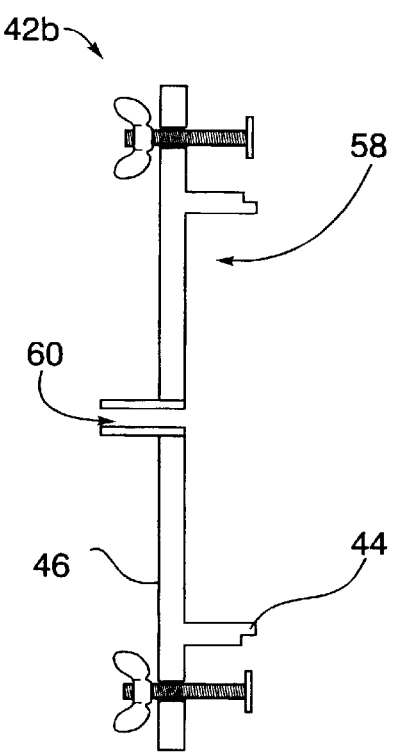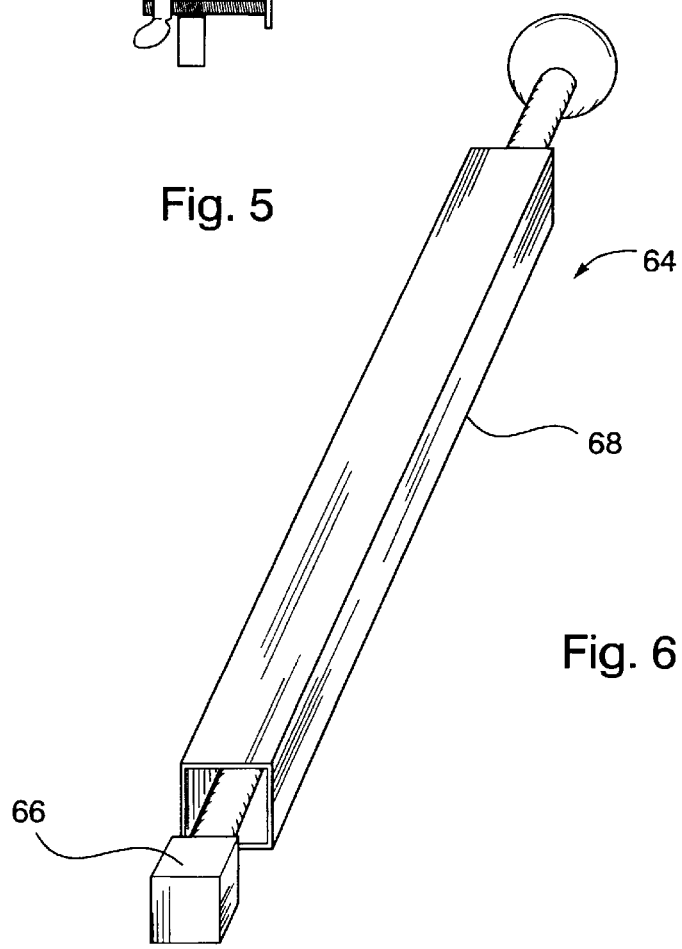
Fig. 4
Fig. 5
Fig. 6

MULTI-DIRECTIONAL PERMEAMETER

BACKGROUND OF THE INVENTION

1. Field of the Invention

The present invention relates generally to a permeameter and more particularly to a multi-directional permeameter which allows water flow to occur either vertically, horizontally or simultaneously vertically and horizontally. This multi-directional flow pattern will render an apparatus which provides a more applicable, representative reading of the coefficients of permeability for the material that is being tested.

2. Description of the Prior Art

Permeameters are known in the art and are used for testing various soils. The use of this permeameter will establish the representative values of the coefficients of permeability of the soil being tested. Through the permeameter, the results should establish how the material will behave in a particular environment, such as through natural deposits or when used as sub-grades in a pavement structure. Unfortunately, conventional permeameters only test flow in a single direction, specifically in a vertical flow pattern. This means of testing limits the results and does not provide a true representative value for the coefficient of permeability for the material which is being tested.

Accordingly, it is seen that previous permeameters are limited in directional flow and thus do not provide the benefits intended with the present invention, such as providing an apparatus which can provide a more applicable, representative reading of the coefficients of permeability for the material being tested, by allowing testing to occur vertically, horizontally, or simultaneously vertically and horizontally. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention is a multi-directional permeameter apparatus that is designed and configured to test soil. The purpose of the apparatus is to determine the coefficients of permeability by utilizing a constant (or falling) head method for the laminar flow of a fluid, such as water, through a specific material or sample which is being tested.

This apparatus is designed and configured to test a sample for the intent of establishing representative values of the coefficients of permeability of the particular sample that may occur with various types of soils, such as, but not limited to, natural deposits, soil placed in embankments, or soil used as sub-grades in a pavement structure. Since the samples are remolded, consolidation is not considered and settlement is normally insignificant.

Additionally, this apparatus of the present invention can also be used for compaction, thereby, allowing the material to be compacted and layered according to conventional test specifications, easily and conveniently. Compaction will occur prior to testing for values of the coefficient of permeability of the compacted sample.

The multi-directional permeameter apparatus of the present invention comprises a base member and a chamber. The chamber is also known as the mold and when secured to the base, it is used for either compaction of material or testing for the permeability of the particular sample.

The base member includes an upper section and a lower section. Extending upwardly from the upper section of the base is a pair of parallel disposed extending shafts. These extending shafts include conventional attaching means. The conventional attaching means will allow the chamber or mold to be removably secured to the base. The upper portion of the base can include a receiving means.

During compaction, a metal plate can be placed over (or in) the receiving means. During testing, a porous plate will be inserted therein. This indentation will provide for the top surface of the base to align with the top surface of the porous plate. This alignment will ease in the placement and attachment of the chamber to the base and may inherently decrease the possibility of leakage during the testing process.

The base further includes a drainage port. The drainage port can extend from the receiving means to the exterior of the base and can also include a means for receiving and maintaining a conventional hose. A conventional valve may optionally be located within the port. This valve will allow for the port to open and close, thereby providing a means for controlling the fluid flow. If a valve is not utilized, then a clamp can be removably secured to the conduit.

The chamber or mold is substantially rectangular in shape and includes an open top, an open bottom and apertures extending through two side walls. Preferably, the apertures on the side walls are oppositely located and are in alignment with one another. A securing means is preferably located on the walls which do not include apertures. The securing means is conventional and is designed and configured to engage with the securing means located on the extending shafts.

A lid is designed to be removably secured to the open top of the chamber and is used during the testing process. This lid further includes a pressure bleed-off valve, which is used when the sample is saturated, prior to testing.

Interchangeable cover plates are adapted to be removably secured to the apertures of the side walls. Confining cover plates are used during compaction and holding cover plates are used during saturation and testing. These holding plates are fabricated from a substantially durable material, such as metal, and are used to hold and maintain a porous stone during testing. The lid and holding cover plates each include a port that is designed and configured to receive and maintain a conduit. Each conduit can include a clamp which is used to initiate or terminate fluid flow into and/or out of the chamber during the saturation and/or testing process. Optionally, each port can be equipped with a conventional valve for allowing the user to merely open or close the port for controlling fluid flow therethrough.

To utilize the apparatus of the present invention, the sample to be tested must be compacted to the required density. This process is known as compaction.

Compaction is established by placing the metal plate on the top surface or in the receiving means of the base. The opened bottom of the mold is placed on the exposed metal plate and is secured to the base by using the securing means located on the shafts of the base and on the side walls of the chamber. Once secured, a paper filter is placed inside the chamber and on the metal base. Confining cover plates are secured to the apertures located in the side wall of the chamber. Attachment of the confining cover plates to the chamber is accomplished via conventional securing means.

The material is then compacted to the required density. For example, in a typical sand sample, the material is placed within the chamber in five equal layers. Each layer is compacted with approximately fifty-six blows with a ten pound hammer having an eighteen inch drop.

After compaction, the top surface of the sample is smoothed off evenly so that the volume may be calculated. Measurements are taken from the top of the sample to the top of the chamber. The average measurement is subtracted from the total length of the chamber, so that the volume can be accurately calculated. After compaction, the mold is removed from the base to enable the material and mold to be weighed. The weight of the mold is subtracted from the composite weight to determine the weight of the sample.

When compaction has been completed, the sample can be prepared for testing for the coefficient of permeability. For preparation, the paper filter is removed and confining cover plate is replaced by the holding cover plate. A new paper filter is placed on the porous stone material. The confining plates are removed from the side wall and are replaced with holding cover plates. Each holding cover plate includes a porous stone. Prior to attachment, a paper filter is inserted into the interior of each holding cover plate. This will provide for the filter to face the sample located within the chamber. A sealant can be used around the porous stone and chamber as well as around each stone plate cover and aperture. This sealant is to prevent water from escaping the chamber during the testing process.

Dependent on the material, such as the use of clay, a swell plate can be placed on top of the compacted material.

The lid is then attached to the open top of the chamber for sealing in the sample, and if used, the swell plate. A void or spacing will be located between the top of the sample and the bottom surface of the lid or between the top of the swell plate and the bottom surface of the lid when a swell plate is used. The lid is secured to the chamber via conventional securing means. This lid can be secured directly to the chamber and/or to the extending shafts of the base. A sealant can also be utilized around the lid in order to prevent a leakage during the testing process.

If a sealant has been used, it must dry prior to testing. Once the sealant has dried sufficiently, testing can commence.

It is noted that when the device is used for testing, a porous stone and filter can be located on the upper surface of the sample. This arrangement will provide for a porous stone and filter to be found at each inlet and outlet. The stone and filter are standard components used during the conventional testing method.

For testing, a conventional method is utilized. In this method a reservoir is filled to a pre-determined level with a fluid, such as water. This reservoir is located above the apparatus of the present invention. This reservoir must maintain water at a pre-determined level and is known as a constant (or falling) head. A fluid source and an outlet means are coupled to the constant (or falling) head. This will allow more water to fill or leave the reservoir as needed. Alternatively, a reservoir of sufficient capacity, and marked with graduations (such as a burette) may be filled with the testing fluid. The reservoir must have an orifice on its lower extreme which will permit the fluid to exit the reservoir, flow through a conduit and enter the port on the lid of the apparatus. The fluid volume in the reservoir shall decrease to a predetermined amount or until a specified time has elapsed, after which the port on the lid shall be closed. This is known as a "falling head". It is noted that the tests described above are known in the art and are utilized to do standard testing of materials for determining the coefficient of permeability for the tested sample.

A first conduit or first hose is coupled to the constant (or falling) head and to the input port located on the lid. A second conduit or second hose is coupled to the constant (or falling) head and to a port located on a side holding cover plate. The first and second ports act as inlets and allow fluid to enter into the device. The first port will render a vertical fluid flow while the second port will render a horizontal fluid flow. A corresponding outlet is provided for each inlet. Accordingly, a third port coupled to a third conduit or third hose is located opposite from the first port, thereby providing for the third port to be secured to the lower portion of the chamber or optionally to the base. A fourth port having a fourth conduit or fourth hose attached thereto is located opposite from the second conduit, thereby providing for the fourth port to be located in the second side of the holding cover plate. Conventional clamps or valves are secured to the ports, conduits or hoses to enable or disable the fluid flow in and out of the apparatus of the present invention. The conduits or hoses are attached to their respective ports/conduits when in a closed position. The discharge conduits shall each empty into separate collection reservoirs which have volumetric graduations.

Prior to testing, the sample must be saturated. For saturating the material, the clamp is removed or the valve is opened for the inlet port of the lid. Simultaneously, the fluid source is slowly activated. On the constant head method, this will allow the fluid to maintain the required height as denoted on the reservoir. Excess fluid will escape via the outlet means.

When water escapes the chamber via the pressure valve on the lid, the sample is saturated. On the falling head method, the source reservoir is refilled to the test starting volume. The apparatus is checked for leakage. If none is detected, testing commences.

The tester selects the type of test to be performed on the sample. The user can do a horizontal, vertical or a combination of horizontal and vertical fluid flow test, by merely opening or closing the respective clamps and/or valves. These tests may be constant or falling head types. After testing, the appropriate tabulations are calculated for determining the coefficients of permeability of the sample being tested.

Accordingly, it is the object of the present invention to provide for a multi-directional permeameter apparatus which will overcome the deficiencies, shortcomings, and drawbacks of prior permeameter apparatus and methods thereof.

Yet another object of the present invention is to provide for a versatile multi-directional permeameter which will successfully allow fluid to flow vertically, horizontally or combined vertically and horizontally.

Still another object of the present invention, to be specifically enumerated herein, is to provide a multi-directional permeameter apparatus in accordance with the preceding objects and which will conform to conventional forms of manufacture, be of simple construction and easy to use so as to provide a device that would be economically feasible, long lasting and relatively trouble free in operation, and either fixed or portable.

Although there have been many inventions related to permeameters, none of the inventions have become sufficiently compact as well as provide for testing to occur either horizontally, vertically or both horizontally and vertically. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

FIG. 4 is a side view of the confining cover plate used with the multi-directional permeameter of the present invention during compaction.

FIG. 5 is a side view of the holding cover plate used with the multi-directional permeameter of the present invention during saturation and testing.

FIG. 6 is a perspective of the hammer used during the process of compaction.

Similar reference numerals refer to similar parts throughout the several views of the drawings.

DESCRIPTION OF THE PREFERRED EMBODIMENTS

Figure 1:
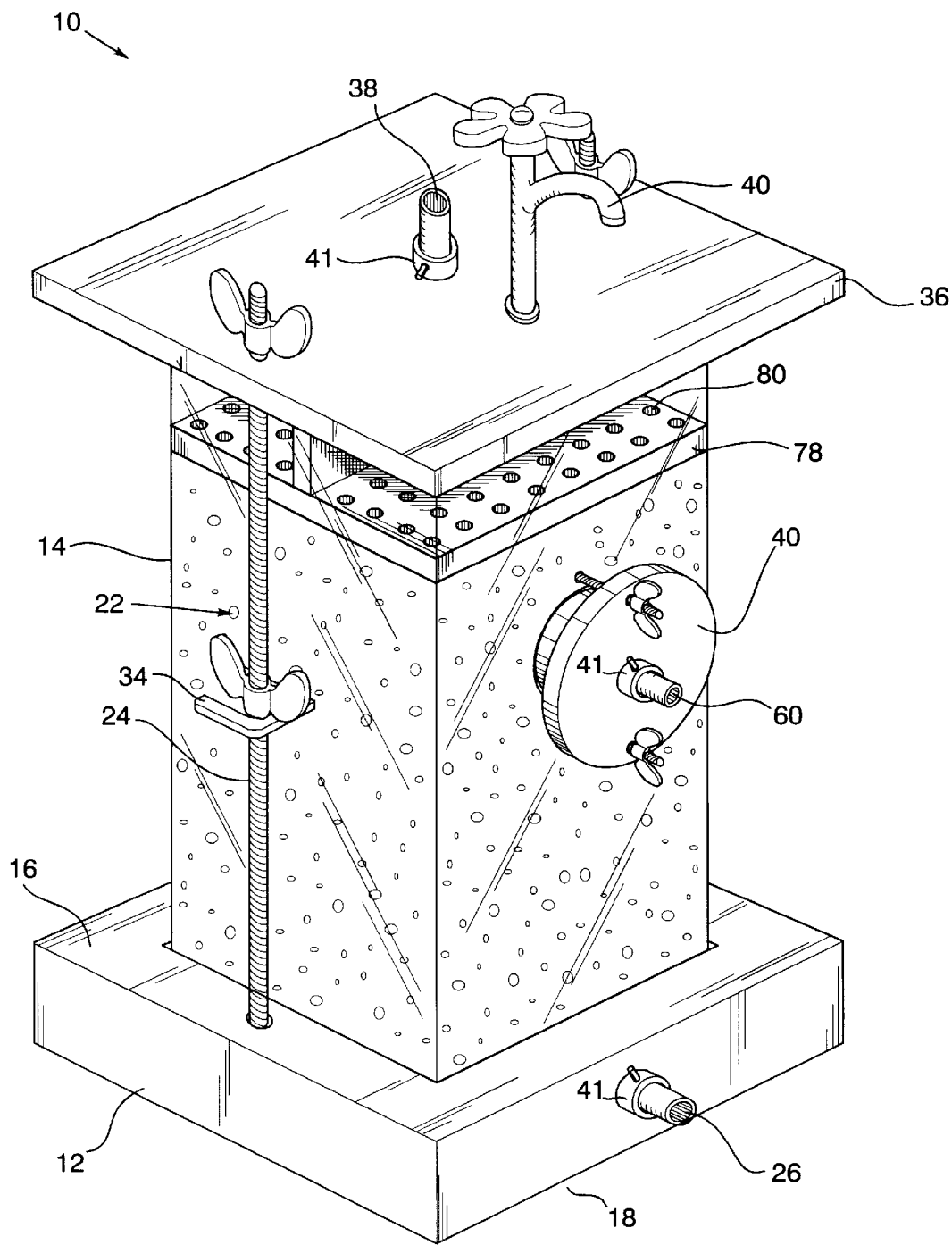
FIG. 1 is a perspective view of the multi-directional permeameter of the present invention.
Figure 2:
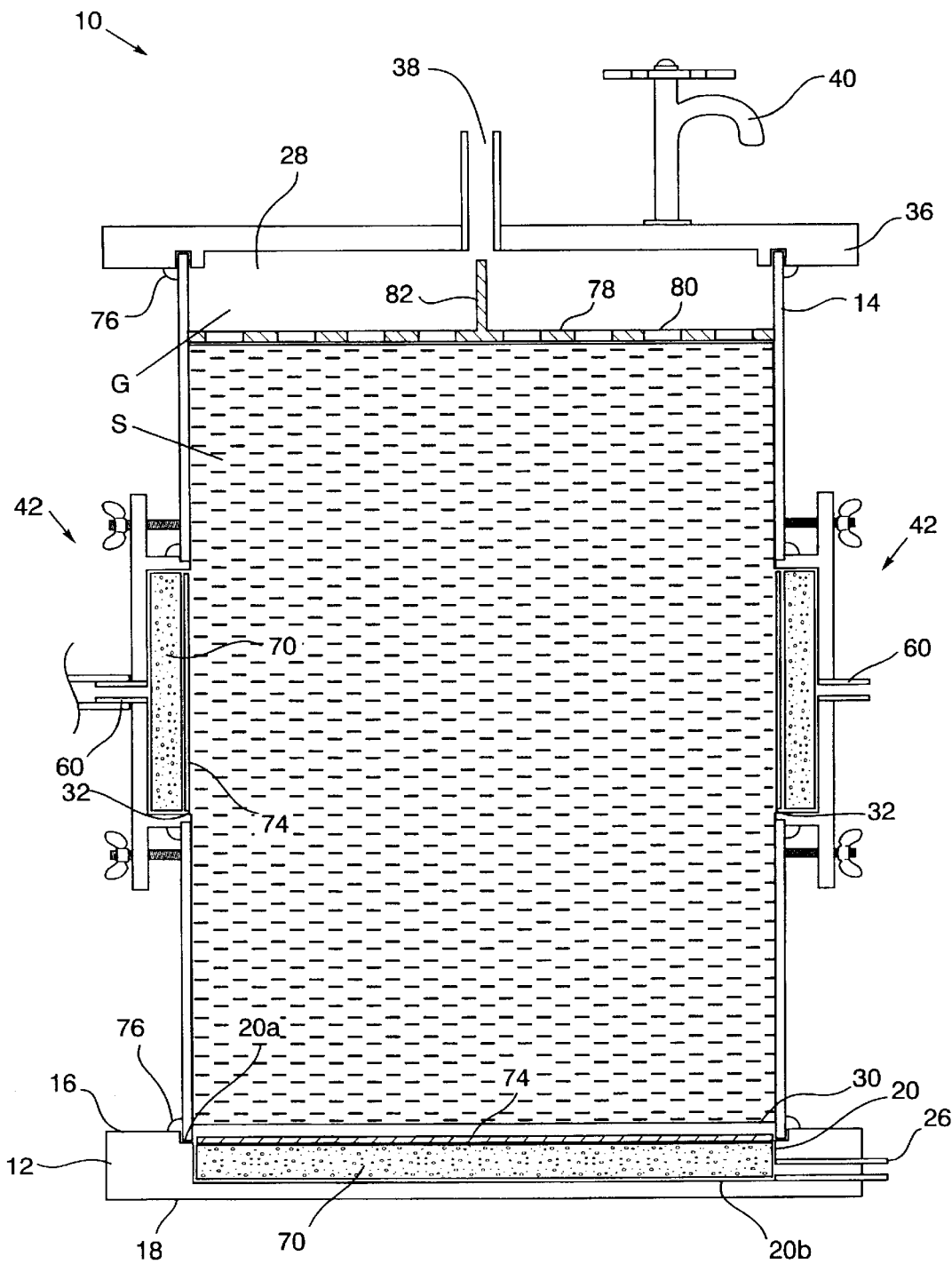
FIG. 2 is a cross sectional view of the multi-directional permeameter of the present invention.
Figure 3:
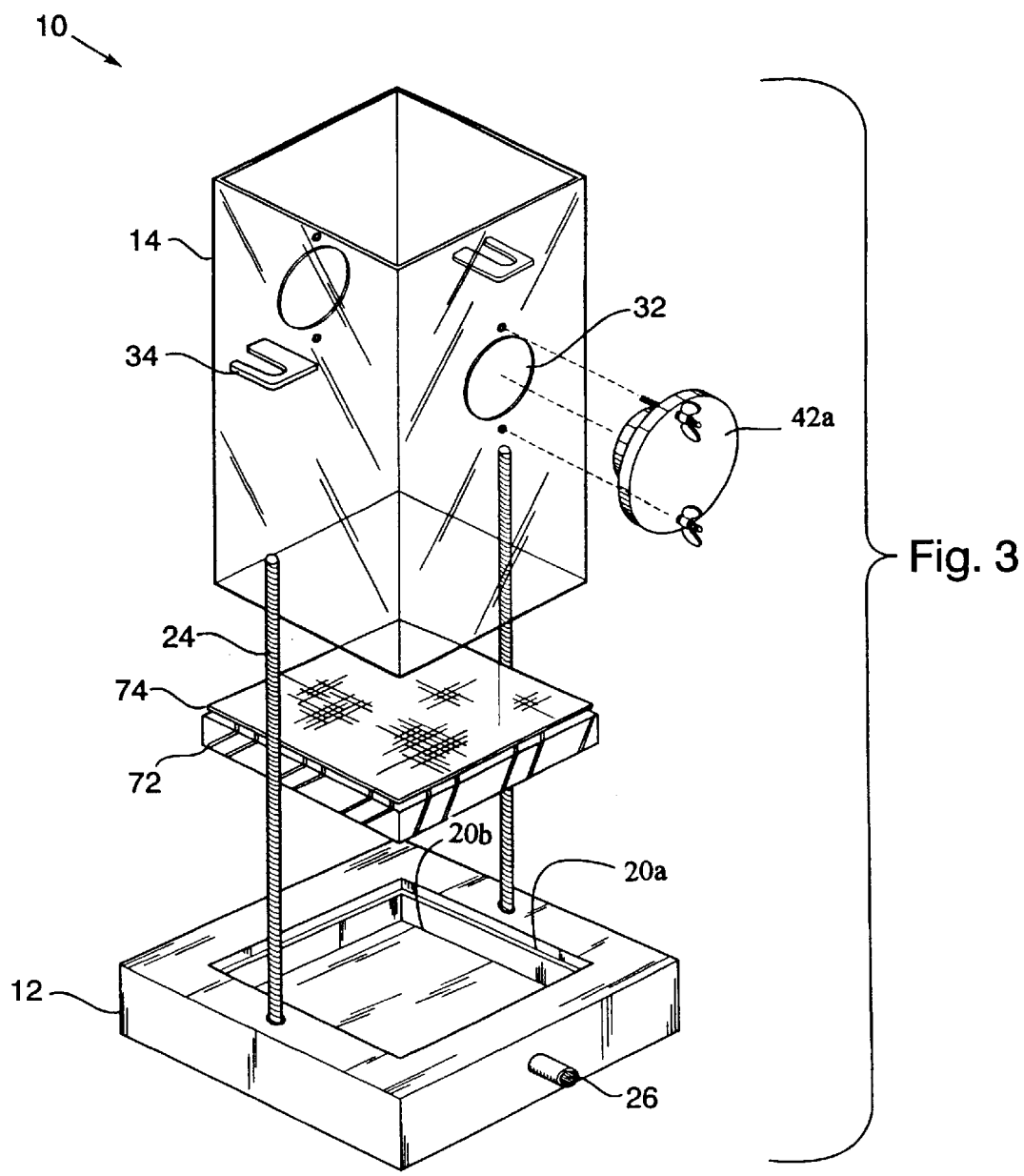
FIG. 3 is an exploded view of the various components of the multi-directional permeameter of the present invention prior to assembly.

With reference to the drawings, and in particular to FIGS. 1, 2 and 3 thereof, the multi-directional permeameter apparatus 10 will be described. The multi-directional permeameter apparatus 10 illustrated and described herein, is used to test soil to determine the coefficients of permeability by utilizing a constant (or falling) head method for the laminar flow of a fluid, such as water, through a specific material or sample which is being tested. Tests using a constant (or falling) head method are known in the art and are conventional tests used for determining the coefficient of permeability of a tested sample. The apparatus 10 of the present invention also prepares the sample prior to testing, by compacting the desired material according to conventional test specifications.

The multi-directional permeameter apparatus 10 of the present invention comprises a base member 12 and a chamber 14. The chamber 14 is also known as the mold and is adapted to be removably secured to the base member 12. The mold includes an interior area which forms and houses a sample S.

This base member 12 further includes an upper section 16 and a lower section 18 (labeled in FIGS. 1 and 2). Located within the upper section 16 is a recess 20. This recess can be stepped, as illustrated in FIGS. 2 and 3, to provide for the uppermost portion 20a of the recess 20 to be larger in width than the lowest portion 20b. This uppermost portion 20a will receive the mold 14 during the testing stage while the lowest portion 20b will receive the porous stone and filter. The use of the steps provides an inherent stop and rest for the chamber and an ideal retaining means for the porous stone and filter.

Extending upwardly from the upper section 16 is a conventional removable attaching means 22. This conventional attaching means enables the chamber 14 to be removably secured to the base 12, easily and quickly. This removability is a necessity when compacting and testing various samples.

The attaching device 22 is conventional and FIGS. 1 and 3 illustrate one type of attaching means 22 which has been utilized to produce favorable results. As seen in the drawings the attaching means 22 comprises a pair of parallel disposed extending threaded shafts 24, an engaging device, illustrated in FIG. 1 and FIG. 3 as C-shaped arms 34, and at least one locking device per shaft. These C-shape arms 34 act a guide device and receive the shafts. At least one locking device is movably located on each shaft. As seen in FIG. 1 and FIG. 3, the locking device is illustrated as a wing nut, thereby securing the chamber or mold 14 to the base 12 by frictionally contacting the guide means 34 as well as frictionally contacting and engaging the upper surface of the lid 36 of the chamber 14. This structure of the attaching device 22 is discussed in further detail when disclosing the process of utilizing the apparatus during compaction and for testing for the coefficients of permeability, as defined below.

The threaded shafts 24 are spaced apart to form a gap therebetween. This gap is of a sufficient distance so as to be non-obtrusive and to permit the user to easily assemble, disassemble, manipulate and utilize the permeameter apparatus 10 and its various components.

Located in the base 12 is a drainage port 26. During testing, fluid is introduced into the attached chamber or mold 14. During the testing process, fluid enters the chamber 14 via the input port 38 and flows through the sample. The fluid then exits the chamber 14 via the output port 26. The volume of fluid which passed through the sample in a predetermined time is used to calculate the coefficient of permeability.

The chamber or mold 14, as illustrated in FIGS. 1–3, is substantially rectangular in shape and includes an open top 28, an open bottom 30 and at least two lateral apertures 32, preferably oppositely located. The chamber or mold is shown to be rectangular, but it is noted that chamber or mold is not limited to this rectangular shape, and can, in fact, include any shape or configuration, so long as to allow fluid to flow within the chamber vertically and horizontally.

A guide 34 can be located on the exterior of the chamber 14. Each guide 34 will receive the shafts 24. As seen the guide 34 comprising C-shaped arms in combination with each shafts 24 and locking device constitutes the attaching device 22. The use of guide means will aid and assist in the directing and steering of the mold 14 on and off of the base 12.

A lid 36 is designed to be removably secured to the open top 28 of the chamber 14 and is used during the testing process. Extending through the lid 36 is an inlet port 38 and a pressure bleed-off valve 40. The inlet port 38 will permit fluid to enter into the chamber while the pressure bleed-off valve will alleviate excess pressure when saturation of the sample S is occurring. Saturation is performed prior to testing, which is later described in further detail. The lid 36 can include a recess portion, illustrated in FIG. 2, but not labeled, to receive the open top of the chamber or mold 14.

For securing the lid 36 to the mold 14, the conventional attaching device 22, as discussed for the base and mold can be utilized. As such, the lid 36 can include arm members, as discussed for the mold or chamber 14. Optionally, and as illustrated in FIG. 1, the lid can extend outwardly from the chamber 14. This will provide for an extended portion to extend beyond the chamber. Orifices, illustrated, but not labeled, can be located through this extended portion. These orifices are used to receive the elongated shafts. Locking device, illustrated as wing nuts, can then be secured and threaded onto the shafts and above the lid for allowing the lid to be frictionally held. The wing nuts will force the lid downward and provide for the lid to be securely fastened onto the chamber.

As seen in FIG. 2, the recess portion, illustrated but not labeled, does provide an easier means for attaching the lid to the chamber. This recess portion will inherently act as a guide for enabling the lid to be secured to the chamber, quickly, easily and efficiently.

It is noted that the attaching device is conventional and can include other alterations and configurations. For example, one alteration would be to change the C-shape of the arm members to a ring shape.

Interchangeable cover plates 42 are adapted to be removably secured to the apertures 32. Two types of cover plates are used with the apparatus of the present invention, dependent on the task which is being performed. Confining cover plates are used during compaction and holding cover plates are used during saturation and testing. Hence, the use of interchangeable cover plates provide for two sets of cover plates. A first set used during compaction and a second set used during testing and saturation.

A confining cover plate 42a is shown in further detail in FIG. 4. As seen in this figure, the confining cover plate 42a is solid and includes a front portion 44 and a rear portion 46. The front portion 44 will be received in the aperture 32 and be aligned with the inner wall of the chamber. As seen in the drawing, the front portion 44 includes a step, illustrated but not labeled, to provide for the step to receive the edge of the aperture. This step will aid and assist in the attachment of the cover plate to the side wall of the chamber. The rear portion 46 is larger in size than the front portion to inherently form a flange. At least one through hole 48 extends through the flange. A conventional securing device 50 is located within the through hole 48. The securing device 50 illustrated in this figure comprises a threaded shaft 52 threadably located within each through hole 48, thereby providing the through hole to be threaded or large enough to pass the threaded shaft through cleanly. The shaft includes a first end and a second end. The first end includes a locking means 54, shown here as a wing nut. The second end can includes a stop 56, insulator, or the like. The stop, insulator or the like will prevent damage to occur to the exterior of the chamber or mold 14, and is fastened securely to the chamber or mold. This confining cover plate can be fabricated from any durable and impenetrable material, such as, but not limited to metals, cured epoxies, polymers, or the like.

The holding cover plate 42b is shown in further detail in FIG. 5. As seen in this figure, the holding cover plate 42b includes a front portion 44 and a rear portion 46. The front portion 44 will be received in the aperture 32 and be aligned with the inner wall of the chamber. This front portion 44 includes a groove 58. This groove will receive a porous stone and filter. Thereby, providing for the holding cover plate to hold and maintain the stone and filter during the testing process. As seen in the drawing, the front portion 44 includes a step, illustrated but not labeled, to provide for the step to receive the edge of the aperture. This step will aid and assist in the attachment of the cover plate to the side wall of the chamber. Extending from the rear portion 46 to the groove 58 is a port 60. The port will enable fluid to enter or exit the chamber. The flanges located at the rear portion 46 are similar in design and structure as the flanges located at the rear portion discussed for the metal cover plate 42a in FIG. 4. As such, these flanges, along with the securing means located at the rear portion will not be described in further detail. The holding cover plate is fabricated from a durable and impenetrable material, such as, but not limited to metals, cured epoxies, polymers, or the like.

Each port located in the base 12, lid 36 and holding cover plates is designed and configured to receive and maintain a conduit. In addition each inlet and outlet can include a water control device, such as a valve 41 (illustrated in FIG. 1) secured to each port, a clamp removably secured to the conduit, or the like. This water control device is used to initiate or terminate fluid flow into and/or out of the chamber during the saturation and/or testing process.

Dependent on the material being tested, such as clay, additional pressure may be needed on its top surface. To achieve this additional pressure, a removable swell plate 78 can be located on the sample S. This swell plate provides adequate pressure on the sample and includes a handle 82. This swell plate fits perfectly and snugly onto the top surface of the sample S. The handle will contact the lower surface of the lid in order to hold the swell plate 78 in place as well as apply the appropriate pressure thereto. As seen in FIG. 2, a space or gap G is located between the lid and sample/swell plate. The swell plate 78 is perforated via openings 80 to permit fluid to flow from the inlet to the sample for saturation. The gap G will fill with water when the sample is appropriately saturated. The excess water will escape via the bleed off valve 40 located on the lid 36.

COMPACTION PROCESS

Generally, the sample S to be tested must be compacted to a specified density. Compaction of a sample S is typically performed prior to testing. During compaction, a metal plate 72, as illustrated in FIG. 3, is placed either over or in the recess 20 of the base 12. In this figure, the metal plate 72 is placed over the recess portion. It is also noted that the plate 72 need not be fabricated from metal and actually can be fabricated from any durable material which is non-absorbent and can withstand the impact which is applied during the process of compaction.

The opened bottom 30 of the mold 14 is placed on the exposed metal plate and is secured to the base 12 by using the attaching means 22. Hence, the shafts 24 will be inserted into the opened portion of the arm member 34. The wing nut will be threaded downwardly and towards the arm member, until contact is made between the arm member 34 and the wing nut. This contact will provide for the wing nut to be in frictional communication with the arm member 34. Once secured, a paper filter is placed inside the chamber 14 and on the metal plate 72. The confining cover plates 42a are secured via securing device 50 to the side apertures 32 located on the wall(s) of the chamber 14.

Compaction of the desired material can commence. For example, in a typical sand sample S, the material is placed within the chamber 14 in five equal layers. Each layer is compacted with approximately fifty-six blows with a ten pound hammer-drop device 64, as illustrated in FIG. 6, having an eighteen inch drop.

For proper compaction, the hammer device 64 must be properly shaped. The proper shape will ensure that the exposed surface area will be compacted appropriately. Hence for a chamber having a rectangular cross-section, the hammer drop 66 and hammer sheath 68 should be designed and configured to be square, as illustrated. For a cylindrical chamber, the hammer drop and hammer sheath should be circular.

After compaction, the top surface of the sample S is smoothed off to provide for the top surface to be even. Evening the top surface will allow the tester to accurately calculate various measures. One measurement is taken from the top of the sample S to the top of the chamber. This measurement is subtracted from the total length of the chamber, so that the volume can be accurately calculated. For calculating the volume (V) the following equation is used.

$$V = bwh \tag{1}$$

where b=the length of the base of the sample S v=the width of the base of the sample S h=height of the sample S It is noted that the equation used for volume is dependent on the shape and configuration of the sample. Hence for alternative shapes, such as cylindrically shaped samples, the equation used for volume calculation will be inherently changed.

After compaction, the mold is removed from the base to enable the material and mold to be weighed. The weight of the mold is a known unit. The metal plate and paper filter are removed. The metal plate is washed and stored for a later use and the paper filter is discarded.

When compaction has been completed, the sample can be prepared for testing for the coefficient of permeability. Prior to testing, the sample S must be saturated.

SATURATION AND TESTING

During saturation and testing, a porous plate 70 will be inserted into the recess 20 of the base 12 and into the grooves 58 of each holding cover plate 42*b*. The recess 20 will provide for the recessed top surface 20*a* of the base 12 to align with the top surface of the porous plate 70. This alignment will ease in the placement and attachment of the chamber 14 to the base 12 and may inherently decrease the possibility of leakage during the testing process.

A new paper filter 74 is placed on the porous stone material 70. Paper filters 74 are also placed on the porous stones located in the cover plate 42*b*. Each filter will face the interior of the chamber 14 and contact the outer surface of the sample.

The chamber 14, having the sample S therein, is placed into the recess 20 so as to be located in the uppermost section 20*a* of the recess. The holding cover plates 42*b* having a porous stone and filter therein are secured to each aperture 32 located on the side(s) of the chamber 14.

To prevent water from escaping the chamber at the various attaching device, a sealant 76, such as latex or silicone caulk, can be used around the base 12 and chamber 14 as well as around each cover plate 42*b* and aperture 32, and at the lid 36 interface with the chamber 14.

Dependent on the material, such as the use of clay, a swell plate 78 can be placed on top of the compacted sample S. If a swell plate is not used, then an additional porous stone and filter will be located between the sample and the lid. This will provide for a porous stone and filter to be located at each inlet and outlet.

The lid 36 is then attached to the open top 28 of the chamber 14 for sealing in the sample S, and if used, the swell plate 78. A void or spacing G will be located between the top of the filter and stone and the bottom surface of the lid 36 or between the top of the swell plate 78 and the bottom surface of the lid when the swell plate is used. The lid 36 is secured to the chamber via conventional attaching implements 22. A sealant can also be utilized around the lid in order to prevent a leakage during the testing process.

If a sealant has been used, it must dry sufficiently prior to testing. Once the sealant has dried, testing can commence.

It is noted that O-rings, gaskets, or other conventional sealing device can be used in place of the sealant in order to provide a unit which is water proof. Optionally, the sealing device can further encompass any known conventional sealing device, such as allowing the chamber, lid, and or cover plates to be threadably secured to its respective component. This will provide both a securing means and a sealing device.

For saturation and testing, a conventional method is utilized. In this method a reservoir is filled to a pre-determined level with a fluid, such as water. This reservoir is located above the apparatus of the present invention. This reservoir must maintain water at a pre-determined level and is known as a constant (or falling) head. A fluid source and an outlet means are coupled to the constant (or falling) head. This will allow more water to fill or leave the reservoir as needed. Alternatively, a reservoir of sufficient capacity, and marked with graduations (such as a burette) may be filled with the testing fluid. The reservoir must have an orifice on its lower extreme which will permit the fluid to exit the reservoir, flow through a conduit and enter the port on the lid of the apparatus. The fluid volume in the reservoir shall decrease to a predetermined amount or until a specified time has elapsed, after which the port on the lid shall be closed. This is known as a "falling head". The tests described above are conventional and known in the art.

A first conduit or first hose is coupled to the constant (or falling) head and to the input port 38 located on the lid 36. A second conduit or second hose (partially illustrated in FIG. 2, but not labeled) is coupled to the constant (or falling) head and to a port 60 located on a holding cover plate. The first and second ports act as inlets and allow fluid to enter into the chamber 14. The first port will render a vertical fluid flow while the second port will render a horizontal fluid flow. A corresponding outlet is provided for each inlet. Accordingly, a third port or drainage port 26 is coupled to a third conduit or third hose is located opposite from the first port, thereby providing for the third port to be secured to the lower portion of the chamber or optionally to the base. This drainage port 26 is shown as being located in the base 12. A fourth port 60 having a fourth conduit or fourth hose attached thereto is located opposite from the second conduit, thereby providing for the fourth port to be located on the second holding cover plate. Conventional clamps or valves are secured to the conduits or hoses to enable or disable the fluid flow in and out of the apparatus of the present invention. The conduits or hoses are attached to their respective ports/conduits when in a closed position. It is noted that conduits for the outlet are optional, and are not truly necessary for successfully employing the invention. In any case, the discharged fluid from each port is collected separately, each in a graduated collection reservoir.

Prior to testing, the sample S must be saturated. For saturating the material, the clamp is removed or the valve is opened for the inlet port of the lid. Simultaneously, the fluid source is slowly activated. This will allow the fluid to maintain the required height as denoted on the reservoir. Excess fluid will escape via the outlet means.

When water escapes the chamber via the pressure bleed-off valve 40 on the lid 36, the sample S is saturated and the pressure bleed-off valve 40 is closed. The apparatus 10 is checked for leakage. If none is detected, testing commences.

The tester selects the type of test to be performed on the sample S. The user can do a horizontal, vertical or a combination of simultaneous horizontal and vertical fluid flow test, by merely opening or closing the respective clamps and/or valves. Testing may be performed using the constant head or falling head method. After testing, the appropriate tabulations are calculated for determining the coefficients of permeability of the sample S being tested.

Prior to calculating the coefficient of permeability, the cross-sectional area for the fluid flow pattern is determined. The cross sectional area for the vertical fluid flow will be the cross sectional area of the shape of the container, since gravity will provide for the fluid to flow through the entire sample, downwardly. For the mold as illustrated in the figures, the cross sectional area will be for a rectangular sample, hence the cross sectional area (A) is as follows:

$$A = lw \quad (2)$$

where l=the length of the base of the sample S w=the width of the base of the sample S As stated previously, the cross-sectional area for fluid flow is dependent upon the shape and structure of the chamber. Equation 2, as defined above, is for a chamber having a rectangular configuration. For one having a circular configuration, the following equation is used for determining the area (A):

$$A = \frac{\pi D_1^2}{4} \quad (3a)$$

where $D_1$=the diameter of the sample S during vertical testing

For horizontal flow, the cross-sectional area is the area of fluid flow. In horizontal flow, this cross sectional area will be the cross-sectional area of the outlet. Hence for a rectangular or square aperture, equation (2) as defined above would be defined as the length (l) and width (w) of the opening. For a circular opening, the following equation is used:

$$A = \frac{D_2^2}{4} \quad (3b)$$

where $D_2$=the diameter of the aperture (outlet) during horizontal testing

The chamber, as stated previously, can include any shape or configuration. Like the chamber, the openings, including the openings used for the inlet and outlet ports for the vertical flow pattern, can have any shape or configuration. Accordingly, the equations for the cross sectional area will change, and may not be the equation as defined in equations (2), (3a) and (3b). Hence, it is the users discretion to determine the appropriate and proper equation for determining and solving for the cross-sectional area.

Examples - Determination off the Coefficients of Permeability for Various Samples
SAMPLE 1 - HORIZONTAL TESTING (Using side ports) - CONSTANT HEAD TEST

| TIME | MINUTES | DISCHARGE | TEMPERATURE |
|------|---------|-----------|-------------|
| 2:45 | 0 | 0 | 72 DEGREES F. |
| 2:46 | 1 | 2 | 72 DEGREES F. |
| 2:47 | 2 | 5 | 72 DEGREES F. |
| 2:48 | 3 | 6 | 72 DEGREES F. |
| 2:49 | 4 | 8 | 72 DEGREES F. |
| 2:50 | 5 | 10 | 72 DEGREES F. |
| 2:55 | 10 | 17 | 72 DEGREES F. |
| 3:00 | 15 | 22 | 72 DEGREES F. |
| 3:05 | 20 | 33 | 72 DEGREES F. |
| 3:10 | 25 | 45 | 72 DEGREES F. |
| 3:15 | 30 | 53 | 72 DEGREES F. |
| 3:20 | 35 | 63 | 72 DEGREES F. |
| 3:25 | 40 | 72 | 72 DEGREES F. |
| 3:30 | 45 | 82 | 72 DEGREES F. |
| 3:35 | 50 | 91 | 72 DEGREES F. |
| 3:40 | 55 | 100 | 72 DEGREES F. |

| | |
|---|---|
| Constant head | 97.8 cm |
| Sample Length | 13.51 cm |
| Aperture diameter | 7.62 cm |
| Area | 45.6 cm² (using eq. (3b)) |
| Weight of Sample and mold | 18.96 lbs. |
| Weight of mold | 5.67 lbs. |
| Weight of Sample | 13.29 lbs. |

The calculation for the coefficient of permeability can be calculated by using the following equation:

$$K_T = \frac{QL}{thA} \quad (4)$$

wherein:

$K_T$=Coefficient of Permeability at T temperature

Q=Total Discharged (cm³)

L=Length of soil Sample t=Total time in seconds h=Total head (constant head)

A=Calculated cross-sectional area of the path of the fluid flow

Using equation (4) the coefficient of permeability for sample 1 is equal to $9.2 \times 10^{-5}$ cm/second.

SAMPLE 2 - VERTICAL TESTING (Using port in lid and base - CONSTANT HEAD TEST

| TIME | MINUTES | DISCHARGE | TEMPERATURE |
|------|---------|-----------|-------------|
| 1:45 | 0 | 0 | 72 DEGREES F. |
| 1:46 | 1 | 5 | 72 DEGREES F. |
| 1:47 | 2 | 8 | 72 DEGREES F. |
| 1:48 | 3 | 11 | 72 DEGREES F. |
| 1:49 | 4 | 14 | 72 DEGREES F. |
| 1:50 | 5 | 18 | 72 DEGREES F. |
| 1:55 | 10 | 32 | 72 DEGREES F. |
| 2:00 | 15 | 48 | 72 DEGREES F. |
| 2:05 | 20 | 64 | 72 DEGREES F. |
| 2:10 | 25 | 78 | 72 DEGREES F. |
| 2:15 | 30 | 93 | 72 DEGREES F. |
| 2:20 | 35 | 110 | 72 DEGREES F. |
| 2:25 | 40 | 124 | 72 DEGREES F. |
| 2:30 | 45 | 140 | 72 DEGREES F. |
| 2:35 | 50 | 154 | 72 DEGREES F. |
| 2:40 | 55 | 169 | 72 DEGREES F. |

| | |
|---|---|
| Constant head | 109.22 cm |
| Sample Height | 17.78 cm |
| Sample Length | 17.78 cm |

-continued

SAMPLE 2 - VERTICAL TESTING (Using port in lid and base - CONSTANT HEAD TEST)

| | |
|---|---|
| Sample width | 13.5 cm |
| Area | 182.25 cm² (using eq. (2)) |
| Weight of Sample and mold | 18.96 lbs. |
| Weight of mold | 5.67 lbs. |
| Weight of Sample | 13.29 lbs. |

Using equation (4) the calculated coefficient of permeability for sample two is $4.6 \times 10^{-5}$ cm/second SAMPLE 3 - VERTICAL AND HORIZONTAL TESTING (Using ALL ports) CONSTANT HEAD TEST

| TIME | MINUTES | DISCHARGE HORIZONTAL | DISCHARGE VERTICAL | TEMPERATURE |
|---|---|---|---|---|
| 3:40 | 0 | 0 | 0 | 72 DEGREES F. |
| 3:41 | 1 | 2 | 3 | 72 DEGREES F. |
| 3:42 | 2 | 5 | 6 | 72 DEGREES F. |
| 3:43 | 3 | 6 | 9 | 72 DEGREES F. |
| 3:44 | 4 | 7 | 10 | 72 DEGREES F. |
| 3:45 | 5 | 8 | 12 | 72 DEGREES F. |
| 3:50 | 10 | 15 | 22 | 72 DEGREES F. |
| 3:55 | 15 | 21 | 32 | 72 DEGREES F. |
| 4:00 | 20 | 28 | 41 | 72 DEGREES F. |
| 4:05 | 25 | 35 | 50 | 72 DEGREES F. |
| 4:10 | 30 | 41 | 60 | 72 DEGREES F. |
| 4:15 | 35 | 48 | 69 | 72 DEGREES F. |
| 4:20 | 40 | 55 | 78 | 72 DEGREES F. |
| 4:25 | 45 | 62 | 87 | 72 DEGREES F. |
| 4:30 | 50 | 68 | 97 | 72 DEGREES F. |
| 4:35 | 55 | 75 | 108 | 72 DEGREES F. |

| | |
|---|---|
| Constant head (Vertical) | 109.22 cm |
| Constant head (Horizontal) | 97.80 cm |
| Weight of Sample and mold | 18.96 lbs. |
| Weight of mold | 5.67 lbs. |
| Weight of Sample | 13.29 lbs. |
| HORIZONTAL DIMENSIONS | |
| Sample Length | 13.51 cm |
| Diameter of outlet (aperture) | 7.62 cm |
| Area | 45.6 cm² (using eq. (3b)) |
| VERTICAL DIMENSIONS | |
| Sample Height | 17.78 cm |
| Sample Length | 17.78 cm |
| Sample width | 13.5 cm |
| Area | 182.25 cm² (using eq. (2)) |

Using equation (4) the horizontal and vertical measurements for the coefficient of permeability is calculated as:

(Horizontal) $6.9 \times 10^{-5}$ cm/second (Vertical) $2.9 \times 10^{-5}$ cm/second Accordingly, it is seen that rendering either vertical, horizontal, or both vertical and horizontal readings for a sample will render results which are more applicable and representative for the material being tested. As can be seen from the results, a more accurate and applicable reading is shown. These results illustrate the true fluid flow pattern when soil is naturally saturated in its own environment. Such information is invaluable, especially in the creation of roads and the like, for providing engineers with the proper tools for adequately designing road or the like, by enabling the designer to properly anticipate any type of situation, weather or the like, which may occur.

While the invention has been particularly shown and described with reference to an embodiment thereof, it will be understood by those skilled in the art that various changes in form and detail may be made without departing from the spirit and scope of the invention.

We claim:

1. A permeameter to be used in combination with a sample for the determination of the coefficient of permeability of the sample being tested, said permeameter comprises:
    a base;
    a chamber having a top which is open;
    an attaching device removably secures said chamber to said base, said base being located opposite from said top of said chamber and providing for said top and said base to be at a true vertical;
    said chamber includes an interior for housing a sample;
    a lid is removably secured to said top and said top is adapted to receive said sample and to provide for said sample to be disposed vertically;
    an inlet port is horizontally disposed in said chamber;
    an outlet port is horizontally disposed in said chamber;
    a first porous material is located between said inlet port and said sample and a second porous material is located between said outlet port and said sample;
    said inlet port and said outlet port permit fluid to enter into and exit out of said chamber horizontally during a testing process for enabling various measurements to occur and allowing retrieval of various information for enabling said measures and said information to be used for the calculation of a coefficient of permeability of said sample in a horizontal plane.

2. A permeameter as in claim 1 wherein a second inlet port is extends through said lid to provide for an inlet to be vertically disposed in said chamber, said chamber includes an open bottom, a second outlet port is vertically disposed in said base, said second inlet port and said second outlet port permit fluid to enter into and exit out of said chamber vertically, a third porous material is located between said second inlet port and said sample and a fourth porous material is located between said second outlet and said sample.

3. A permeameter as in claim 2 wherein said inlet port and said outlet port includes a control device to terminate or permit the flow of a fluid into and through said inlet port and said outlet port, said control port operates independently from one another.

4. A permeameter as in claim 2 wherein a third porous material is located between said second inlet port and said sample and a fourth porous material is located between said second outlet and said sample.

5. A permeameter as in claim 4 wherein a first filter is located between said first porous material and said sample, a second filter is located between said second porous material and said sample, a third filter is located between said third porous material and said sample, and a fourth filter is located between said fourth porous material and said sample.

6. A permeameter as in claim 2 wherein a swell plate is removably received within said top of said chamber and provides for said swell plate to be located between said sample and said lid.

7. A permeameter as in claim 1 wherein a first aperture and a second aperture extend horizontally through said chamber, said first aperture and said second aperture constitute a first set of apertures, said inlet port is removably secured to said first aperture and said outlet port is removably secured to said second aperture.

8. A permeameter as in claim 7 wherein said chamber includes an open bottom and said base includes a recess for receiving said open bottom of said chamber.

9. A permeameter as in claim 8 wherein said recess is stepped for providing a first indentation and a second indentation, said first indentation will receive a porous material and said second indentation will receive said chamber and said first indentation is lower than said second indentation.

10. A permeameter as in claim 7 wherein said first aperture and said second aperture each receives a cover plate, said first cover plate and said second cover plate are removably secured to said first aperture and said second aperture, respectively, via a securing device, said first set of apertures are horizontally aligned, said first cover plate includes said inlet port and said first porous material, and said second cover plate includes said outlet port and said second porous material.

11. A permeameter as in claim 10 wherein said first cover plate and said second cover plate constitute a first set of cover plates, said first set of cover plates being holding cover plates, a second set of cover plates are adapted to be removably secured to said first set of apertures, second set being confining cover plates, said confining cover plates being solid and used for compaction.

12. A permeameter as in claim 11 wherein each of said holding cover plates further includes a recess portion, said recess portion receives and maintains said first and said second porous material.

13. A permeameter as in claim 1 wherein said attaching device comprises at least one vertical threaded shaft extending upwardly from said base, and a receiving device extending outwardly from said chamber, said receiving device receives said shafts.

14. A permeameter as in claim 1 wherein said inlet port and said outlet port each include a control device to terminate or permit the flow of a fluid into and through said inlet port and said outlet port.

15. A permeameter as in claim 1 wherein a first filter is located between said first porous material and said sample and a second filter is located between said second porous material and said sample.

16. A permeameter and compaction apparatus adapted to receive a sample for testing and adapted to prepare said sample by compacting said sample, said permeameter and compaction apparatus comprises:

a base;

a chamber having an open top and an open bottom;

an attaching device removably secures said open bottom of said chamber to said base;
said chamber includes an interior for housing a sample for testing and for receiving material for compaction;

a first aperture and a second aperture extend horizontally through said chamber, said first aperture and said second aperture constitute a first set of apertures;

a first set of cover plates are removably secured to said first set of apertures for preventing fluid flow therethrough;

a second set of cover plates are removably secured to said first set of apertures for enabling fluid flow to commence horizontally;

said first set of cover plates are used during a compaction process and said second set of cover plates are used during a testing process;

an inlet port and an outlet port are located in said second set of cover plates for enabling horizontal testing of said sample.

17. A permeameter and compaction apparatus as in claim 16 wherein a lid is removably secured to said open top of said chamber.

18. A permeameter and compaction apparatus as in claim 17 wherein a second inlet port extends through said lid to provide for said second inlet to be vertically disposed in said chamber, a second outlet port is vertically disposed in said base, said second inlet port and said second outlet port permit fluid to enter into and exit out of said chamber vertically.

19. A permeameter and compaction apparatus as in claim 18, during testing said second set of cover plates each include a porous material for providing a first porous material to be located between said inlet port, horizontally disposed, and said sample, a second porous material to be located between said outlet port, horizontally disposed, and said sample, a third porous material is located between said second inlet port and said sample and a fourth porous material is located between said second outlet and said sample.

20. A permeameter and compaction apparatus as in claim 16 wherein said second set of cover plates each include a porous material, and said porous material is located between said sample and said inlet port and said sample and said outlet port, respectively.

* * * * *